United States Patent
Brion et al.

(12)

(10) Patent No.: US 6,433,164 B2
(45) Date of Patent: Aug. 13, 2002

(54) (3,4,7,8,9,10-HEXAHYDRO-6, 10 -6H-PYRIDAZINO [1,2-A] [1,2] DIAZEPINE-1-CARBOXYLIC-ACID DERIVATIVES

(75) Inventors: Francis Brion, Toulouse; Veronique Croco, Dijon; Patrick Roussel, Thiais, all of (FR)

(73) Assignee: Aventis Pharma S.A. (FR)

( * ) Notice: Subject to any disclaimer, the term of this patent is extended or adjusted under 35 U.S.C. 154(b) by 0 days.

(21) Appl. No.: 09/765,761

(22) Filed: Jan. 19, 2001

Related U.S. Application Data

(63) Continuation of application No. 09/296,325, filed on Apr. 22, 1999.

(30) Foreign Application Priority Data

Apr. 27, 1998 (FR) .............................. 98 05242

(51) Int. Cl.[7] ...................... C07D 237/04; C07D 487/04
(52) U.S. Cl. ...................................................... 540/500
(58) Field of Search .......................................... 540/500

(56) References Cited

U.S. PATENT DOCUMENTS

| | | | | | |
|---|---|---|---|---|---|
| 4,512,924 A | * | 4/1985 | Atwood et al. | .......... | 260/243.3 |
| 5,723,602 A | * | 3/1998 | Karabewsky et al. | ....... | 540/500 |

\* cited by examiner

*Primary Examiner*—Bruck Kifle
(74) *Attorney, Agent, or Firm*—Bierman, Muselian and Lucas

(57) ABSTRACT

A compound of the formula

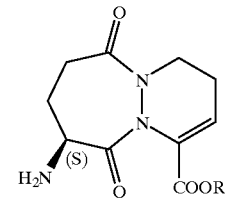

I wherein R is alkyl or aralkyl of up to 18 carbon atoms, the amine function being optionally protected are used to prepare compounds of the formula

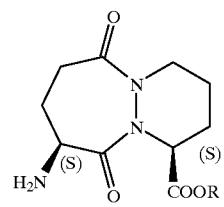

III in which R retains its previous meaning and the amine is optionally protected.

3 Claims, No Drawings

(3,4,7,8,9,10-HEXAHYDRO-6, 10 -6H-PYRIDAZINO [1,2-A] [1,2] DIAZEPINE-1-CARBOXYLIC-ACID DERIVATIVES

This application is a continuation os U.S. Pat. application Ser. No. 09/296,325 filed Apr. 22, 1999.

OBJECTS OF THE INVENTION

It is an object of the invention to provide the novel compounds of formula I and a process and intermediates for their preparation.

It is another object of the invention to provide the novel compounds of formula III and a process for their preparation.

These and other objects and advantages of the invention will become obvious from the following detailed description.

THE INVENTION

The novel compounds of the invention are compounds of the formula

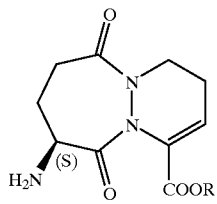

I wherein R is selected from the group consisting of hydrogen, alkyl of 1 to 18 carbon atoms and aryl and aralkyl of up to 18 carbon atoms and the amine is optionally protected.

Examples of R as alkyl are methyl, ethyl, propyl, isopropyl, n-butyl, isobutyl and tert-butyl and as aryl or aralkyl are benzyl and naphthyl.

Preferred compounds of the invention have the formula

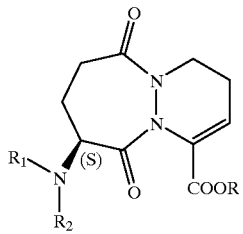

IA wherein A is defined as above, $R_2$ is hydrogen and $R_1$ is selected from the group consisting of

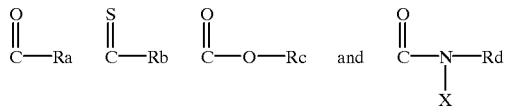

$R_a$, $R_b$, $R_c$ and $R_d$ are individually selected from the group consisting of alkyl of 1 to 18 carbon atoms, aryl and aryl of up to 18 carbon atoms and mono- or polycyclic containing at least one heteroatom and X is selected from the group consisting of hydrogen, alkyl of 1 to 8 carbon atoms and aryl of up to 14 carbon atoms or $R_1$ and $R_2$ together with the nitrogen to which they are attached form a mono- or polycyclic with at least one heteroatom.

Examples of cyclic protective groups are

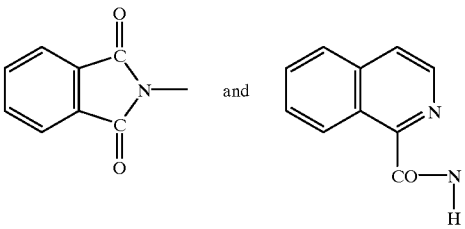

A preferred compound of formula I has the formula

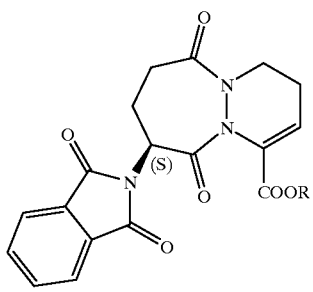

$IA_1$ wherein R is alkyl of 1 to 8 carbon atoms, especially 1,1-dimethylethyl.

The process of the invention for the preparation of a compound of formula I comprises reacting a compound of the formula

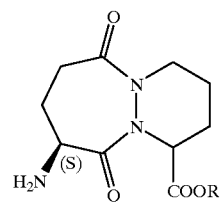

II in racemic form at the 6-member ring and R is as defined and above the amine is protected with a dehydrogenation agent to form the corresponding compound of formula I.

Preferably, the starting material has the formula

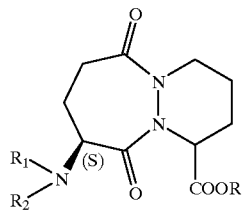

IIA wherein R, $R_1$ and $R_2$ have the above definitions and the dehydrogenation agent is a strong base, an oxidizing agent or a sulfur or selenium derivative.

The compounds of formula II are racemic (SR+SS) at the level of the 6-member ring and are novel products. They can be prepared by the following process.

Préparation a

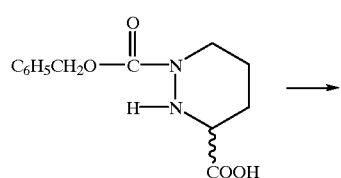

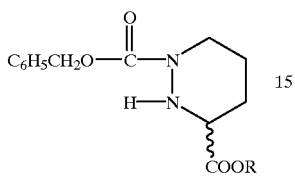

Préparation b

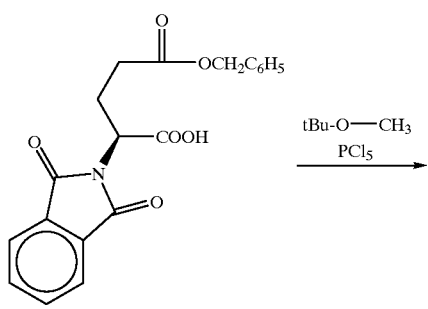

Product of Preparation a
+
Product of Preparation b

CH$_2$Cl$_2$
pyridine

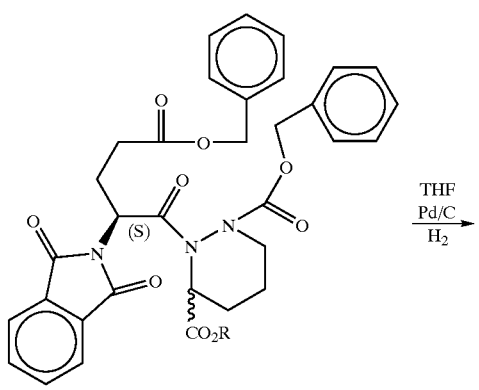

THF
Pd/C
H$_2$

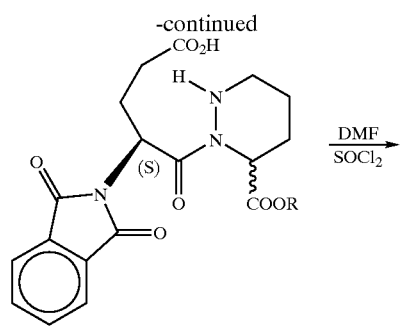

DMF
SOCl$_2$

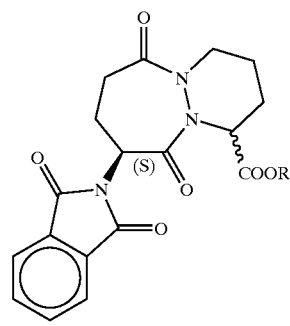

Starting product of Example 1

The starting compounds of the said process are described in or can be prepared as set forth in J. Chem. Soc. Perkins Trans. 1 (1979), Vol. 6, p. 1451–1454 Chem. Soc. Chem. Comm. (1977), p. 635–36.

The process of the invention for the preparation of a compound of the formula

III

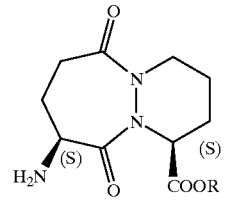

wherein R is defined as above and the amine is optionally protected comprises reacting a compound of formula I with a reducing agent.

Preferably, the resulting compound has the formula

IIIA

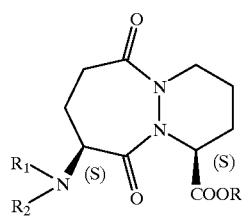

wherein R, R$_1$ and R$_2$ are defined as above and the reducing agent is hydrogen in the presence of Raney nickel, palladium on carbon, palladium dihydroxide in the presence of talc, ruthenium on carbon or rhodium in the presence of aluminum, more preferably hydrogen in the presence of Raney nickel. The reaction is effected in the presence of a solvent such as acetic acid, methanol, ethanol, isopropanol, dimethoxyethane, butanone, DMF or acetonitrile.

The compounds of formula IIIA are intermediates for the preparation of pharmacological products such as the compounds described in EP Patent No. 84,095 and in J. Chem. Soc. Perkin Trans. 1, (1986), p. 1011. Other products of formula II are useful in a similar process.

The products of formula II and IIA in the SR form or the form of a mixture (SR+SS) are novel intermediates as are the compounds of formula III and IIIA with the proviso that R is not hydrogen or tert.-butyl in formula III and in formula IIIA, R is not hydrogen or tert.-butyl when the amine is protected by phthalimido. EP 94,095 describes a compound of formula IIIA when R is tert.-butyl and the amine is phthalimido.

In the following examples, there are described several preferred embodiments to illustrate the invention. However, it is to be understood that the invention is not intended to be limited to the specific embodiments.

PREPARATION 1

1,1-dimethyl-ethyl 9-(1,3-dihydro-1,3-dioxo-2H-isoindol-2-yl)-octahydro-6,10-dioxo-6H-pyridazino[1,2-a][1,2-diazepine-1-carboxylate Preparation a: 1-(benzyl) and 3-(1,1-dimethyl-ethyl) hexahydro-3-(2H)-pyridazinedicarboxylate J. Chem. Soc. Chem. Comm. (1977) p. 635–636 or J. Chem. Soc. Perkin Trans. (1979) Vol 6. p. 1451–1454.

920 μl of $BF_3$-$Et_2O$ and a solution of 18.85 g of terbutyl trichloroacetimidate, 45.5 ml of cyclohexane and 57.5 ml of dichloro methane were introduced at 20° C. into a suspension of 11.50 g of 1,2-benzyl hexahydro-1,3(2H) pyridazinedicarboxylate and 115 ml of dichloromethane. After isolation and purification treatment, the expected product was obtained.

Preparation b: benzyl γ-(chlorocarbonyl)-1,3-dioxo-1H-isoindole-2(3H)-butanoate 30 g of benzyl γ-carboxy-1,3-dioxo-1H-isoindol-(3H)-butanoate (EP 94,095) were introduced, under a nitrogen atmosphere, into 81 ml of terbutylmethylether. The reaction mixture was then cooled to 0°–2° C. and 17 g of phosphorus pentachloride were added. The reaction mixture was allowed to return to ambient temperature and was stirred for 6 hours, concentrated under reduced pressure, taken to 41° C. and the dry extract obtained was entrained using toluene. The product was held at ambient temperature and under a nitrogen atmosphere, then diluted for use in $CH_2Cl_2$, to obtain a 0.5 M solution of the desired product.

Stage A: 1-(benzyl) 3-(1,1-dimethylethyl)-2-[1,5-dioxo-2-(1,3-dioxo-14-isoindol-2(3H)-yl-5-benzyloxy-pentyl]-tetrahydro-1,3-(2H)-pyridazine dicarboxylate A 0.5 M solution of 52 ml of the product of Preparation b in, methylene chloride was cooled to 0°–1° C. and 5.6 g of the product of Preparation a and 22 ml of dichloromethane were added thereto. The reaction mixture was stirred for 3 hours at 0°±1° C. and 1.77 ml of pyridine and 11 ml of methylene chloride were added. The dichloromethane was evaporated under reduced pressure at 30° C., followed by taking up in ethyl acetate, washing with aqueous solutions of sodium chloride and sodium bicarbonate. Extraction was carried out with ethyl acetate, followed by drying, rinsing and extracting under reduced pressure to obtain the desired product which was chromatographed on silica and eluting with a heptane-ethyl acetate mixture 60–40 to obtain 4.697 g of the desired product melting at ≦35° C.

Stage B: γ-[[3-[1,1-dimethylethoxy)carbonyl]-tetrahydro-2(1H)-pyridazinyl]carbonyl]-1,3-dioxo-1H-isoindole-2-(3H)-butanoic acid A mixture of 4.61 g of the product of Stage A and 47 ml of tetrahydrofuran was mixed at 20° C. and the reaction mixture was hydrogenated at ambient temperature, using 400 mg of palladium on carbon as a catalyst. When the reaction was completed, the reaction mixture was filtered and rinsed with THF to obtain 2.76 g of the desired product.

Stage C: 1,1-dimethylethyl 9-(1,3-dihydro-1,3-dioxo-2H-isoindol-2-yl)-octahydro-6,10-dioxo-6H-pyridazino[1,2-a]-1,2-diazepine-1-carboxylate A solution of 0.846 ml of thionyl chloride in 2.6 ml of dichloromethane was added at 0+2° C. to a mixture of 2.6 g of the product of Stage B, 26 ml of methylene chloride and 50 μl of dimethylformamide. The reaction mixture was allowed to return to ambient temperature and was stirred for 6 hours 20 minutes. The isolation and purification operations are carried out to obtain the desired product.

EXAMPLE 1

1,1-dimethylethyl (9S),9-(1,3-dihydro-1,3-dioxopyridazino[1,2-a]-diazepine-1-carboxylate a) Preparation of LDA 7.2 ml of butyllithium were added at about −60° over 10 minutes, under a nitrogen atmosphere with stirring to a mixture of 20 ml of THF and 3.2 ml of diisopropylamine. The temperature was allowed to rise to 0° C., was held for 1 hour at 0° C. and then was returned to −60° C.

b) Preparation of $C_6H_5SeBr$ 0.26 of bromine were added at 10° C. to a solution of 1.88 g of diphenyldiselenium and 6 ml of THF. The reaction mixture was stirred for 1 hour at 20° C.

c) Reaction

A mixture of 3.44 g of 1,2-dimethylethyl (1S-cis) 9-(1,3-dihydro-1,3-dioxo-2H-isoindol-2-yl)-octahydro-6,10-dioxo-6H-pyridazino[1,2-a]-1,2-diazepine-1-carboxylate was cooled at −65° C. and the solution of LDA prepared above was added. The reaction mixture was stirred for 10 minutes and the solution of $C_6H_5SeBr$ was added at a temperature of 60° C.±5° C. The temperature was allowed to return to about 0° C. and 4 ml of water, 1.2 of ml of acetic acid and 4 ml of hydrogen peroxide were added. The temperature was, allowed to rise to 10° C. and the reaction mixture was stirred for 1 hour. Then, 40 ml of a 10% aqueous solution of sodium chloride and 80 ml of ethyl acetate were added. The reaction mixture was decanted, washed with a saturated solution of sodium chloride, and/or sodium bicarbonate at 10%, followed by evaporation under reduced pressure. The resultant mixture was chromatographed on silica, eluting with a methylene chloride-isopropyl ether mixture to obtain 1.3 g of the desired product with a specific rotation of $α_D$=+126.5° C.=0.335/MeOH Use: 1,1-dimethylethyl (1S-cis) 9-(1,3-dihydro-1,3-dioxo-2H-isoindol-2-yl)-octahydro-6,10-dioxo-6H-pyridazino[1,2-a][1,2]-diazepine-1-carboxylate a) Preparation of the Catalyst A mixture of 0.106 g of Raney nickel (Jansen) and 2 ml of sodium hydroxide was stirred for 2 hours at 60° C. and the nickel was washed with water. One drop of acetic acid was added to the last wash water and the nickel was then washed with ethanol and ethyl acetate. The nickel obtained was kept under reduced pressure.

b) Reduction 3 ml of ethyl acetate were added to 0.053 g of nickel prepared as previously and 0.0485 g of the product of Example 1 was added to the suspension obtained. The hydrogenation stage took place at ambient temperature, until there was no further absorption of hydrogen. 2 ml of hydrogen were absorbed and the product had a TLC rf=0.27 eluant isopropyl ether/methylene chloride (50—50).

Various modifications of the products and processes of the invention may be made without departing from the spirit or scope thereof and it is to be understood that the invention is intended to be limited only as defined in the appended claims.

What we claim is:

1. A compound of the formula

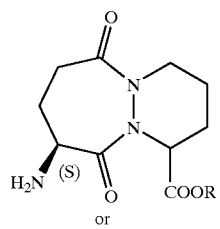

II or

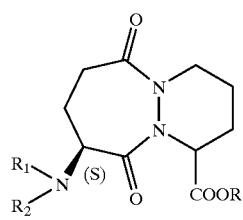

IIA wherein R is selected from the group consisting of hydrogen, alkyl of 1 to 4 carbon atoms and $R_1$ and $R_2$ form phthalimido with the nitrogen in SR form or in (SR+SS) mixture..

2. A compound selected from the group consisting of the formulae

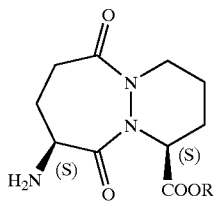

III

-continued
and

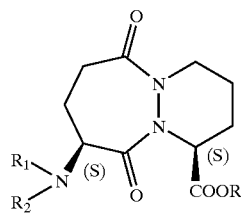

IIIA wherein R is alkyl of 1 to 4 carbon atoms, $R_2$ and $R_1$ with the nitrogen form phthalimido.

3. A process for preparation of a compound of the formula

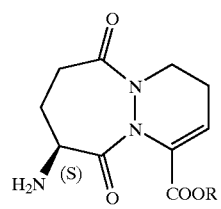

I wherein R is selected from the group consisting of hydrogen, alkyl of 1 to 18 carbon atoms and aryl and aralkyl of up to 18 carbon atoms and the amine is unprotected or protected comprising reacting a compound of the formula

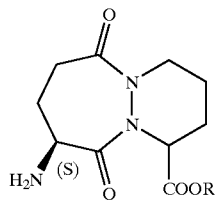

II where the amine is protected with a hydrogenation agent which is a mixture of phenylselenium bromide, hydrogen peroxide and LDA.

* * * * *